United States Patent [19]
Politzer

[11] Patent Number: 4,819,669
[45] Date of Patent: Apr. 11, 1989

[54] METHOD AND APPARATUS FOR SHAVING THE BEARD

[76] Inventor: Eugène J. Politzer, 65, rue Jouffroy, FR-75017 Paris, France

[21] Appl. No.: 943,259

[22] PCT Filed: Apr. 1, 1986

[86] PCT No.: PCT/FR86/00109
§ 371 Date: Nov. 26, 1986
§ 102(e) Date: Nov. 26, 1986

[87] PCT Pub. No.: WO86/05676
PCT Pub. Date: Oct. 9, 1986

[30] Foreign Application Priority Data
Mar. 29, 1985 [FR] France ............................ 8504825
Jun. 12, 1985 [FR] France ............................ 8508860

[51] Int. Cl.⁴ .............................................. A45D 26/00
[52] U.S. Cl. ................................ 132/200; 128/303.18; 132/212; 219/223
[58] Field of Search ....................... 132/9, 118; 17/20; 219/223; 128/303.18

[56] References Cited

U.S. PATENT DOCUMENTS

| | | | |
|---|---|---|---|
| 1,378,137 | 5/1921 | Ross | 132/118 |
| 1,720,775 | 7/1929 | Welden | 132/118 |
| 3,093,724 | 6/1963 | Johnson | 132/118 |
| 3,197,612 | 7/1965 | Reich | 219/223 |
| 3,659,613 | 5/1972 | Bredemeier | 128/395 |
| 3,693,623 | 9/1972 | Harte et al. | 128/303.1 |
| 4,388,924 | 6/1983 | Weissman et al. | 128/303.1 |

FOREIGN PATENT DOCUMENTS

| | | | |
|---|---|---|---|
| 1560498 | 2/1969 | France | 219/223 |
| 2123287 | 2/1984 | United Kingdom | 128/303.18 |

*Primary Examiner*—John J. Wilson
*Attorney, Agent, or Firm*—Steele, Gould & Fried

[57] ABSTRACT

A method of shaving a beard is disclosed which includes the steps of passing the hairs of a beard through an electrically and thermally insulating grid and then applying laser energy of selected wave lengths to the ends of the hairs passing through the grid. Preferably, the energy from the laser source is directed perpendicularly to the hairs in the grid.

2 Claims, 3 Drawing Sheets

METHOD AND APPARATUS FOR SHAVING THE BEARD

The present invention relates to a method of shaving and to apparatus enabling the method to be implemented.

BACKGROUND OF THE INVENTION

From time immemorial, man has removed hair from the surface of the skin initially by using a knife of wood or bone, and subsequently by using a metal blade, either dry or in conjunction with soaps or other products. Electric apparatuses were then designed making use of rotating or vibrating blades placed behind a grille having small openings for dry shaving. Various paths have been followed to find improvements to these means, but nevertheless the results have generally been disappointing.

A limitation on shaving action is established by the impossibility of using blades to go beyond the surface of the epidermis, and consequently the bristles grow back again within a few hours and show up sufficiently for a second shave to be necessary towards the end of the day, particularly for dark haired people.

Patent application No. GB-A-2 123 287 and US-A-3 693 623 have already proposed using an epilation device which includes a laser ray generator of the type developed for medical applications, whose beam is guided by flexible optical fibers so as to be directed onto the roots of individual hairs. This technique takes a long time and is therefore fundamentally incompatible with shaving the beard which in practice requires a set of bristles to be removed rapidly and simultaneously within a limited period of time. In the above-mentioned epilation technique, each hair root must be treated individually. In addition, transmitting a laser beam over optical fibers may cause problems in home applications.

Further, FR-A-1 560 498 proposes singeing hairs under the action of the impacts from sparks which strike the hairs lengthwise. However, in addition to the problem of rapid head wear due to spark formation, this solution has not proved satisfactory.

The object of the present invention is to mitigate these drawbacks.

SUMMARY OF THE INVENTION

According to the present invention, the method of shaving is characterized in that it consists in applying thermal energy to the top ends of a set of hairs passing through a very fine grille of electrically and thermally insulating material, so as to apply said energy over the entire length of the hairs to be removed, thereby singeing them.

It is common observation that hairs singe in a fraction of a second, for example when barbers apply a flame to the ends of cut hairs. In contrast to what might have been thought, such singeing is practically imperceptible to the skin. This fact may be observed by rapidly passing the flame of a match tengentially near the back of a hand or an arm. The hairs are consumed right into the pores without the epidermis suffering from any burning sensation. Several hours must then elapse before the hairs reappear at epidermis level, i.e. up to the level which is obtained immediately after shaving with a blade. Removing hair by combustion goes deeper than eliminating it by shaving to skin level since singeing continues into the pores, thereby making it possible to reduce the frequency of shaving by a factor of about 2, since a blade can only act above the surface of the epidermis. In addition, the act of shaving by singeing is comparable to a rubbing out motion which is considerably quicker than the present conventional shaving techniques. Finally, there is no need to replace worn blades as is necessary with current apparatuses.

In a first implementation, the method of shaving the beard without using a blade makes use of energy delivered by a laser source and is characterized in that the light energy emitted by the source is caused to impact on the top ends of a set of hairs emerging from the skin in order to cause a singeing thermal effect on said ends, which effect extends over the entire length of the hairs right into the pores beneath the epidermis.

In accordance with the new shaving technique, use is made of the thermal energy of light radiation which is conveyed in a properly limited manner to the ends of hairs to be shaved by using a laser beam whose operating parameters: power and pulse duration are designed as a function of the distance from the surface of the epidermis. This process, which makes use of the properties of laser beams, and in particular instantaneous desiccation, combustion, volatilization, and pulverization enables hairs to be removed by singeing down to a shallow depth inside the pores of the epidermis.

The distance between the impact of the laser beam and the skin is determined by the position of the very fine grille through which the hairs to be removed are passed, thus determining a shaving width of a few centimeters by suitably scanning the beam.

In accordance with the invention, use is made of a laser ray emitting source (a $CO_2$ laser, an excimer laser) including devices for adjusting the temperature by adjusting the power used in conjunction with a shaver head.

According to another characteristic of the invention radiation from a helium-neon laser is used.

According to another feature of the invention, the power required at the hairs lies in the range 0.5 W to 3 W.

The required application of heat may also be obtained by instantaneous contact with a set of points on a heater wire.

In a second implementation, the shaving method is characterized in that it consists in applying the ends of the hairs against discontinuous heater surfaces for very short periods of time. This implementation is based on the phenomenon of heat accumulating at the tips of a wire which is corrugated or which, in more general terms, includes projections from its longitudinal direction.

From the point of view of the shaving method, both implementations are equivalent since they serve to convey the heat energy required to obtain singeing at a desired location.

The time of contact between the end of a hair passing through the very fine grille and a heating surface may be about one millisecond, for example.

The present invention also provides shaving apparatus for performing the method and characterized in that it comprises a body provided with a working head including a cover having at least one expanded protection element for engaging hairs and standing them up inside the head, where said hairs are subjected to singeing by the action of a corrugated wire.

According to another feature of the invention, the apparatus for performing the method is characterized in that inside the body it includes an electric motor capable of being connected to a power supply with the motor shaft driving a finned turbine.

According to another characteristic of the invention, the corrugated heater wire has a series of teeth or projections.

Thus, by virtue of this characteristic, the heating power may be reduced by heat accumulation at the tips of the teeth according to a point effect, with the tips of the teeth being raised to dull red. There is no danger of burning the skin, only the hairs which pass through the grille are singed. Since the rotor rotates at a speed of several thousand revolutions per minute (r.p.m.) the fins cool the grill, thereby increasing the safety of the shaving apparatus in use.

Other characteristics and advantages of the invention appear from the following description of a particular implementation given by way of non-limiting example with reference to the drawings, in which:

DESCRIPTION OF THE PREFERRED EMBODIMENTS OF THE INVENTION

Figure 1:
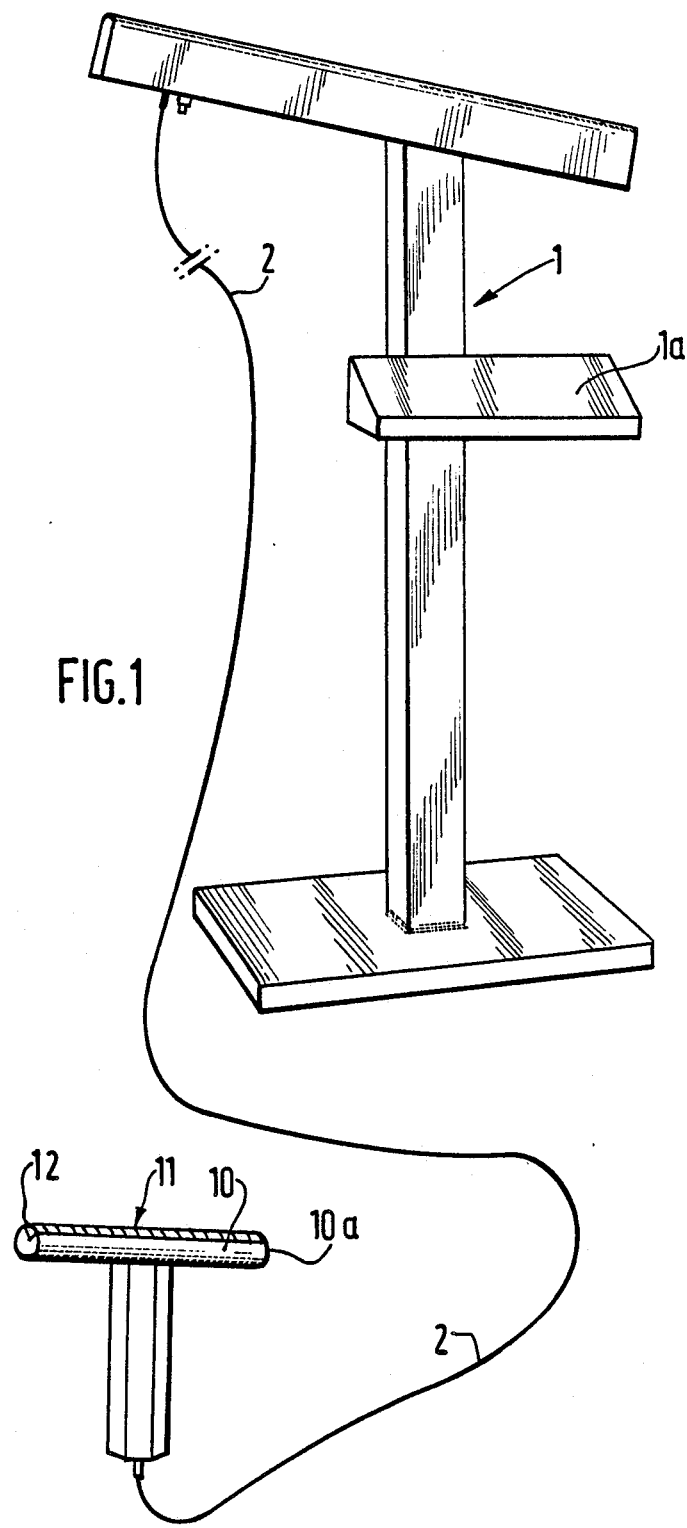
FIG. 1 is a perspective view of an apparatus including a continuous laser shaving head.

In FIG. 1 which shows a device in accordance with a first embodiment, there can be seen a shaver head for shaving by means of a laser light beam and suitable for being connected by a flexible cord to a radio frequency (RF) supply.

FIG. 1 is a perspective view of an apparatus including a shaving head having a laser which is continuous or which may be interrupted by using a shutter which is rotated or reciprocated back-and-forth by a scanning system, thereby preventing the temperature from rising, which system may optionally lead to the initial power delivered being modified, for example by acting on focusing.

The shaver device is constituted by an assembly 1 for providing radio frequency (RF) power and connected by a flexible cord 2 to a shaver head 10 including a miniaturized laser, i.e. to an item which is capable of being held in the hand by the user.

FIG. 1 also shows a shaver head 1 which is T-shaped having a slot 11 along one of its generator lines 10a to pass laser radiation over a width of a few centimeters.

Such a head 10 which constitutes the laser block may be cooled in a manner known per se by a cooling device (using turbine or fins or others), with a very fine mesh grille 12 of insulating material (for example of Capton) being interposed between the skin and the laser effect on the ends of the hairs.

This shaver head exploits guided light propagation inside the head 10 using an appropriate scanning system, thereby forming a laser guide which is easily maneuvered even by a nonspecialist who can thereby guide low power radiation, said system being provided with a suitable device for preventing heating of the skin and possible damage to the eyes. Under such conditions, the shaver cover constitutes a mask preventing laser radiation from emerging. Advantageously, a safety contact is provided on the cover preventing laser emission when the cover is not in place.

It should be emphasized that the light beam may be emitted continuously or intermittently, and that it may be static or moving using a rotary screen placed inside the head or using a screen subjected to reciprocating motion. These various forms of motion are generally obtained by means of a small electric motor and a very low power mechanical or magnetic transmission.

The equipment for feeding the laser head with radio frequency RF is mounted either on a fixed support 1, or else on a moving support capable of being readily displaced from a main power supply which is generally AC at 220 volts or 250 volts and which is then rectified by a static rectifier. A control and adjustment desk 1a is used for switching the shaver on and off.

By applying the head 10, it is thus possible to remove a beard properly in a very short period of time, while avoiding the need for the man to shave repeatedly since he remains well shaved for a much longer period than when using conventional systems.

Although the types of laser mentioned above are presently the most advantageous, since they operate in the necessary power range of 0.5W to 3W, it is also possible to use a helium-neon laser having a power which is greater than that currently available from said type of laser.

Miniaturization may be used to provide an integrated and independent power supply so that the entire assembly is of size comparable to a present shaver.

Figure 2:
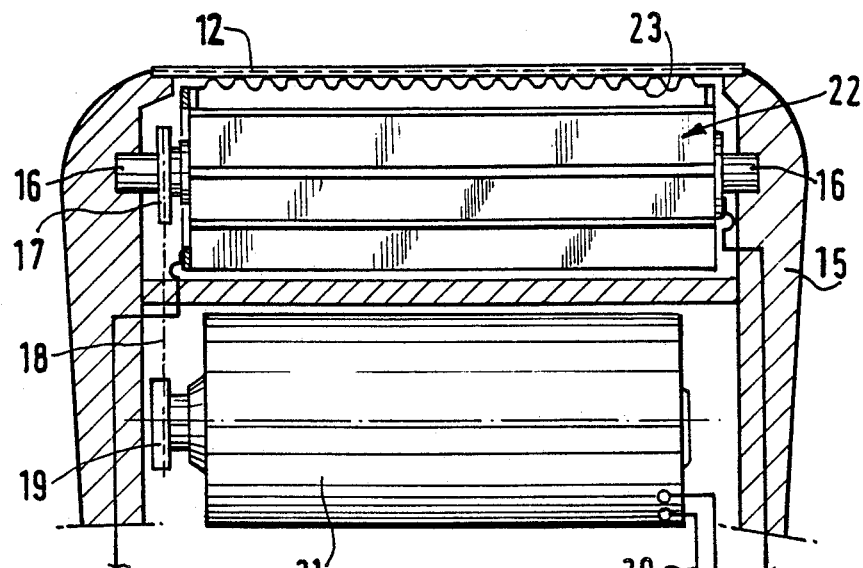
FIG. 2 is a section through an apparatus in accordance with a second embodiment.

FIG. 2 shows a thermal effect shaver with a body 15 made of two molded half-shells which are assembled by conventional means such as screws, for example. The body 15 has an inside cavity mounting an electric motor 21 connected to a suitable electricity power supply 20 and driving a rotor or turbine 22. The rotor 22 rotates inside the body 15, being supported on integrally molded bearings 16, with one of the two ends of the rotor shaft having a pulley wheel 17 over which a belt 18 is passed, with the belt also passing round a hub 19 mounted on the shaft of the motor 21.

The rotor 22 is essentially constituted by a set of fins 24 which are preferably made of insulating material. At least one of the fins has a corrugated heater wire 23 running along its outer periphery.

Figure 4:
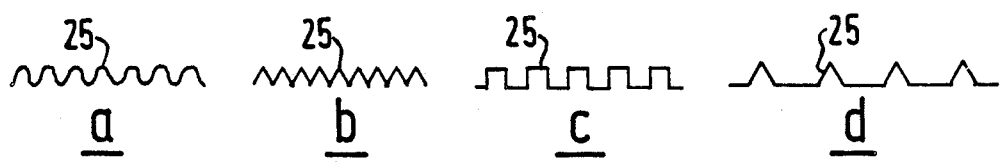
FIG. 4 shows various ways in which the heater wire may be corrugated.

In accordance with a characteristic of the invention, the corrugated heater wire 23 is not straight but has a succession of teeth or the like 25. Various types of teeth are shown in FIG. 4. In FIG. 4a the teeth are generally sinusoidal. In FIG. 4b, the teeth are in the form of saw teeth. In FIG. 4c the teeth are constituted by a square shape, and in FIG. 4d, the teeth are triangular. Any other shape of tooth may be used, but it is important in accordance with the invention for there to be peaks or ridges along the length of the corrugated heater wire 23 in order to allow heat to accumulate thereon. This is the active part of the corrugated thermal wire and, as mentioned above, the peaks are heated to dull red.

Figure 3:
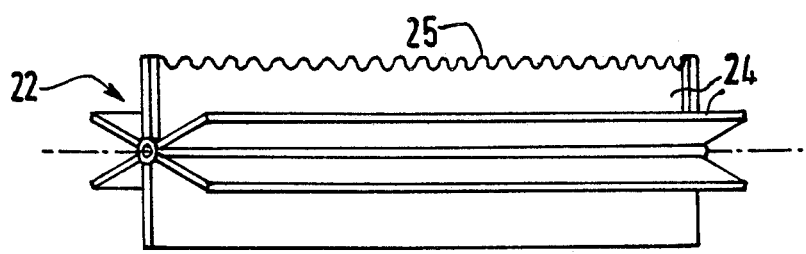
FIG. 3 is a perspective view of a rotor.

As can be seen in FIG. 3, the corrugated heater wire 23 passes close to the grille 12. Naturally the grille has very fine holes therethrough and it is advantageously made of insulating material. As in conventional electric shaving, hairs penetrate into the inside of the grille and they are brought into contact for a very short duration with the corrugated wire 25 which causes them to be singed down to the roots.

The corrugated heater wire 23 may be fed with DC or with AC given the effect of thermal inertia. It may be connected either directly to mains, optionally via a rechargeable battery, or else to a hand-operated dynamo as for some kinds of flashlamp.

When the rotor 22 is made of insulating material, the corrugated heater wire 23 is powered by means of rotary contacts 13 and 17 connected to a power supply 21, with the rotary contacts pressing against the ends of the turbine 22. These ends are connected to opposite ends of the corrugated heater wire 23. Naturally, the rotor and its fins churn the air as they rotate, thereby constantly cooling the grille which thus remains at ambient temperature. Preferably, the grille or the top portion of the cover are removable so as to enable singed hair to be removed.

Although the above description has been given by way of example, showing only one corrugated heater wire 23 on the rotor 22, it is naturally possible to dispose similar corrugated heater wires on at least some of the other fins and to power them in a squirrel-cage manner so as to increase the operating frequency of the apparatus.

Figure 5:
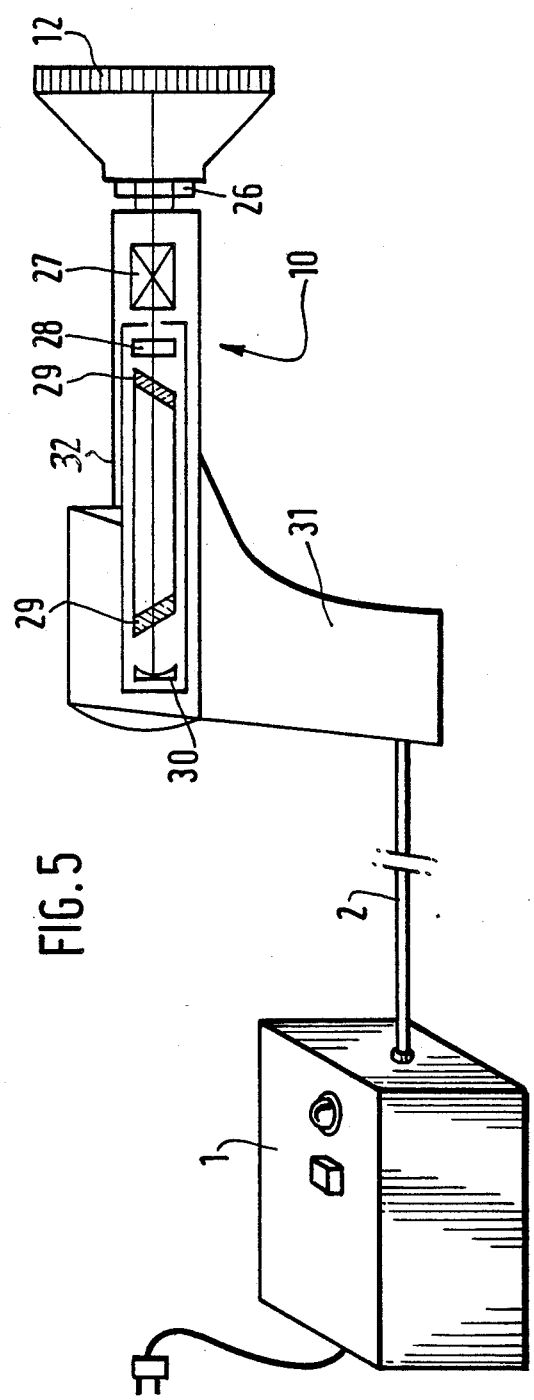
FIG. 5 shows a shaver made in accordance with the first embodiment.

FIG. 5 shows a laser shaver in accordance with the first embodiment. This shaver comprises, as described with reference to FIG. 1, a power supply block 1 connected by an electric cord 2 to the head 10. As before, the head comprises a grille 12 made of plastic material of the CAPTON type which is pivotally mounted at 26 about the axis of the laser head in order to follow the contours of the face. The laser head 10 includes a handle 31 fixed to a tube 32. The tubular cavity defined by the tube 32 includes a cavity having a gas disposed between Brewster angle faces 29 disposed between two mirrors 28 and 30. At the output from the laser per se, there is a scanning device 27 for deflecting the beam so that in a very short period of time it scans over the surface of the grille 12 through which the hairs of the beard to be removed are passed.

I claim:

1. A method of shaving a beard, comprising the steps of:
    passing hairs of the beard through an electrically and thermally insulating grid; and,
    applying energy delivered by a laser source of selected wave lengths to the ends of the hairs passing through the grid, whereby the hairs are singed along their entire length, and thereby eliminated.
2. The method of claim 2, comprising the step of directing the energy from the laser source in a beam aligned substantially perpendicularly to the hairs in the grid.

* * * * *

UNITED STATES PATENT AND TRADEMARK OFFICE
CERTIFICATE OF CORRECTION

PATENT NO. : 4,819,669

DATED : April 11, 1989

INVENTOR(S) : Eugene J. Politzer

It is certified that error appears in the above-identified patent and that said Letters Patent is hereby corrected as shown below:

Column 1, line 60: please delete "tengentially"

and insert-"tangentially"--therefor

Column 6, line 23: please delete --"2"-- and insert --"1"--therefor

Signed and Sealed this

Sixth Day of March, 1990

Attest:

JEFFREY M. SAMUELS

Attesting Officer

Acting Commissioner of Patents and Trademarks